US007973157B2

(12) United States Patent
Major et al.

(10) Patent No.: US 7,973,157 B2
(45) Date of Patent: Jul. 5, 2011

(54) IMINO AND AMINO SUGAR PURIFICATION

(75) Inventors: Michael Major, Mequon, WI (US); Robert Peterson, Germantown, WI (US); Szymon Kosinski, Menomonee Falls, WI (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 11/450,978

(22) Filed: Jun. 8, 2006

(65) Prior Publication Data
US 2006/0293515 A1    Dec. 28, 2006

Related U.S. Application Data

(60) Provisional application No. 60/689,130, filed on Jun. 8, 2005.

(51) Int. Cl.
C08B 37/00 (2006.01)
C07H 5/04 (2006.01)
C07H 5/06 (2006.01)

(52) U.S. Cl. ....................................... 536/55.3

(58) Field of Classification Search ........................ None
See application file for complete search history.

(56) References Cited

U.S. PATENT DOCUMENTS

| 2,801,261 | A | * | 7/1957 | Hornberger, Jr. ............... 558/11 |
| 4,634,765 | A | | 1/1987 | Liu |
| 4,639,436 | A | | 1/1987 | Junge et al. |
| 5,003,072 | A | | 3/1991 | Partis et al. |
| 5,043,273 | A | | 8/1991 | Scudder et al. |
| 5,071,990 | A | | 12/1991 | Hinsken |
| 5,144,037 | A | | 9/1992 | Partis et al. |
| 5,153,318 | A | | 10/1992 | Rideout et al. |
| 5,157,116 | A | | 10/1992 | Nucep et al. |
| 5,192,772 | A | | 3/1993 | Yoshikuni et al. |
| 5,200,523 | A | | 4/1993 | Fleet |
| 5,206,251 | A | | 4/1993 | Khanna et al. |
| 5,248,779 | A | | 9/1993 | Fleet |
| 5,258,518 | A | | 11/1993 | Khanna et al. |
| 5,268,482 | A | | 12/1993 | Koszyk et al. |
| 5,273,981 | A | | 12/1993 | Getman et al. |
| 5,451,679 | A | | 9/1995 | Barta et al. |
| 5,622,972 | A | * | 4/1997 | Bryant et al. ............... 514/315 |
| 6,462,197 | B2 | | 10/2002 | Hollingsworth et al. |
| 6,620,921 | B1 | | 9/2003 | Furneaux et al. |
| 6,683,185 | B2 | | 1/2004 | Hollingsworth et al. |
| 6,809,083 | B1 | | 10/2004 | Mueller et al. |
| 2004/0063973 | A1 | | 4/2004 | Benjes et al. |

FOREIGN PATENT DOCUMENTS

| AU | 737579 | 12/1998 |
| WO | WO01/10429 | 2/2001 |

OTHER PUBLICATIONS

Mills, Encyclopedia of Reagents for Organic Synthesis, Hydrochloric Acid, 2001 John Wily & Sons.*
Joseph, Carbohydrate Research 337 (2002) 1083-1087.*
Lamb, Laboratory Manual of General Chemistry, Harvard University Press, 1916, p. 108.*
Kinast et al. Angew. Chem. Int. Ed. Engl. 20 (1998), No. 9, pp. 805-806.*
Uriel et al., A Short and Efficient Synthesis of 1,5-dideoxy-1,5-imino-D-galactitol (1-deoxy-D-galactostatin) and 1,5-dideoxy-1,5-dideoxy-1,5-imino-L-altritol (1-deoxy-L-altrostatin) From D-galactose, Synlett (1999), vol. 5, pp. 593-595.
Chernois, "Semimicro Experimental Organic Chemistry," J. de Graff (1958), pp. 31-48.
Linden et al., "1-Deoxynojirimycin Hydrochloride," Acta ChrystallographicaC50, pp. 746-749, 1994.
Amat et al., "Eantioselective Synthesis of 1-deoxy-D-gluonojirimycin From A Phenylglycinol Derived Lactam," Tetrahedron Letters, pp. 5355-5358, 2004.
Encyclopedia of Chemical Technology, 4th Ed., 1995, John Wiley & Sons, vol. 14: p. 737-741.
Heiker et al., 1990, "Synthesis of D-*galacto*-1-deoxynojirimycin (1,5-dideoxy-1, 5-imino-D-galactitol) starting from 1-deoxynojirimycin," Carbohydrate Research, vol. 203: p. 314-318.
Supplementary European Search Report dated Mar. 11, 2010 issued in corresponding European Patent Application No. EP 06 77 2888.
Mellor et al., Preparation, biochemical characterization and biological properties of radiolabelled N-alkylated deoxynojirimycins, Biochem. J. Aug. 15, 2002; 366(Pt 1):225-233.
Santoyo-Gonzalez et al., "Use of N-Pivaloyl Imidazole as Protective Reagent for Sugars." Synthesis 1998 1787-1792.
Heiker et al., "Synthesis of D-galacto-1-deoxynojirimycin (1, 5-dideoxy-1, 5-imino-D-galactitol) starting from 1-deoxynojirimycin." Carbohydrate Research, 203: 314-318, 1990.
Schuller et al., "Synthesis of 2-acetamido-1, 2-dideoxy-D-galactonojirimycin (2-acetamido-1, 2, 5-trideoxy-1, 5-imino-D-galacitol) from 1-deoxynojirimycin." Carbohydrate Res. 1990; 203: 308-313.

* cited by examiner

Primary Examiner — Layla Bland
(74) Attorney, Agent, or Firm — Hoffmann & Baron, LLP

(57) ABSTRACT

Novel processes for the purification of an imino or amino sugar, such as D-1-deoxygalactonojirimycin (DGJ). Particularly, there are described processes for the purification of multi-kilogram scale sugars using hydrochloric acid.

20 Claims, 6 Drawing Sheets

IMINO AND AMINO SUGAR PURIFICATION

This application claims priority from U.S. Provisional Patent Application Ser. No. 60/689,130, filed on Jun. 8, 2005, the disclosure of which is herein incorporated by reference in its entirety.

BACKGROUND OF THE INVENTION

This invention relates to a process for purification of imino or amino sugars, such as D-1-deoxygalactonojirimycin hydrochloride (DGJ.HCl). This process can be used to produce multi-kilogram amounts of these nitrogen-containing sugars.

Sugars are useful in pharmacology since, in multiple biological processes, they have been found to play a major role in the selective inhibition of various enzymatic functions. One important type of sugars is the glycosidase inhibitors, which are useful in treatment of metabolic disorders. Galactosidases catalyze the hydrolysis of glycosidic linkages and are important in the metabolism of complex carbohydrates. Galactosidase inhibitors, such as D-1-deoxygalactonojirimycin (DGJ), can be used in the treatment of many diseases and conditions, including diabetes (e.g., U.S. Pat. No. 4,634,765), cancer (e.g., U.S. Pat. No. 5,250,545), herpes (e.g.,U.S. Pat. No. 4,957,926), HIV and Fabry Disease (Fan et al.,*Nat. Med.* 1999 5:1, 112-5).

Commonly, sugars are purified through chromatographic separation. This can be done quickly and efficiently for laboratory scale synthesis, however, column chromatography and similar separation techniques become less useful as larger amounts of sugar are purified. The size of the column, amount of solvents and stationary phase (e.g. silica gel) required and time needed for separation each increase with the amount of product purified, making purification from multi-kilogram scale synthesis unrealistic using column chromatography.

Another common purification technique for sugars uses an ion-exchange resin. This technique can be tedious, requiring a tedious pre-treatment of the ion exchange resin. The available ion exchange resins are also not necessarily able to separate the sugars from salts (e.g.,NaCl). Acidic resins tend to remove both metal ions found in the crude product and amino- or imino-sugars from the solution and are therefore not useful. Finding a resin that can selectively remove the metal cations and leave amino- or imino-sugars in solution is not trivial. In addition, after purification of a sugar using an ion exchange resin, an additional step of concentrating the diluted aqueous solution is required. This step can cause decomposition of the sugar, which produces contaminants, and reduces the yield.

U.S. Pat. Nos. 6,740,780, 6,683,185, 6,653,482, 6,653,480, 6,649,766, 6,605,724, 6,590,121, and 6,462,197 describe a process for the preparation of imino-sugars. These compounds are generally prepared from hydroxyl-protected oxime intermediates by formation of a lactam that is reduced to the hexitol. However, this process has disadvantages for the production on a multi-kg scale with regard to safety, upscaling, handling, and synthesis complexity. For example, several of the disclosed syntheses use flash chromatography for purification or ion-exchange resin treatment, a procedure that is not practicable on larger scale.

One particularly useful imino sugar is DGJ. There are several DGJ preparations disclosed in publications, most of which are not suitable for an industrial laboratory on a preparative scale (e.g., >100 g). One such synthesis include a synthesis from D-galactose (Santoyo-Gonzalez, et al., *Synlett* 1999 593-595; *Synthesis* 1998 1787-1792), in which the use of chromatography is taught for the purification of the DGJ as well as for the purification of DGJ intermediates. The use of ion exchange resins for the purification of DGJ is also disclosed, but there is no indication of which, if any, resin would be a viable for the purification of DGJ on a preparative scale. The largest scale of DGJ prepared published is 13 g (see Fred-Robert Heiker, Alfred Matthias Schueller, *Carbohydrate Research*, 1990; 203: 314-318). In this publication, DGJ was isolated by stirring with ion-exchange resin Lewatit MP 400(OH$^-$) and crystallized with ethanol. However, this process cannot be readily scaled to multi-kilogram quantities.

Similarly, other industrial and pharmaceutically useful sugars are commonly purified using chromatography and ion exchange resins that cannot easily be scaled up to the purification of multi-kilogram quantities.

Therefore, there is a need for a process for purifying nitrogen-containing sugars, preferably hexose amino- or iminosugars that is simple and cost effective for large-scale synthesis.

SUMMARY OF THE INVENTION

It has now been discovered that nitrogen-containing sugars, i.e., amino- or imino-sugars can be efficiently provided in a large-scale process by treating the crude amino- or iminosugar with concentrated hydrochloric acid. No pretreatment or dilution is needed, such as that required when ion-exchange resins are used for purification. Nitrogen-containing sugars are soluble and stable enough in concentrated HCl. Therefore, HCl can be used to separate the sugar from insoluble alkali and alkali earth metal chlorides (e.g., NaCl) in a simple, fast, and effective process.

These alkali and alkali earth metal chlorides are formed from other alkali and alkali earth metal containing compositions that may be used in one of the steps of amino- or imino-sugars synthesis for various purposes, e.g., protecting group removal. The HCl treatment can be used to remove other impurities not soluble in hydrochloric acid. In the synthesis of amino- or imino-sugars, the alkali and alkali earth metal containing compositions have to be removed in the final purification of desired amino- or imino-sugar. One example of use of alkali and alkali earth metal-containing compounds is the use of bases to remove acyl-protecting groups during the syntheses of amino- or imino-sugars. For example, sodium methoxide in methanol is used in the last step of DGJ synthesis as a catalyst in a transesterification reaction to remove pivaloyl-protecting groups.

Other features, advantages, and embodiments of the invention will be apparent to those skilled in the art from the following description, accompanying data and appended claims.

BRIEF DESCRIPTION OF THE DRAWINGS

The following drawings form part of the present specification and are included to demonstrate further certain aspects of the invention. The invention may be better understood by reference to one or more of these drawings in combination with the detailed description of specific embodiments presented herein.

DETAILED DESCRIPTION OF PREFERRED EMBODIMENTS

Figure 1:
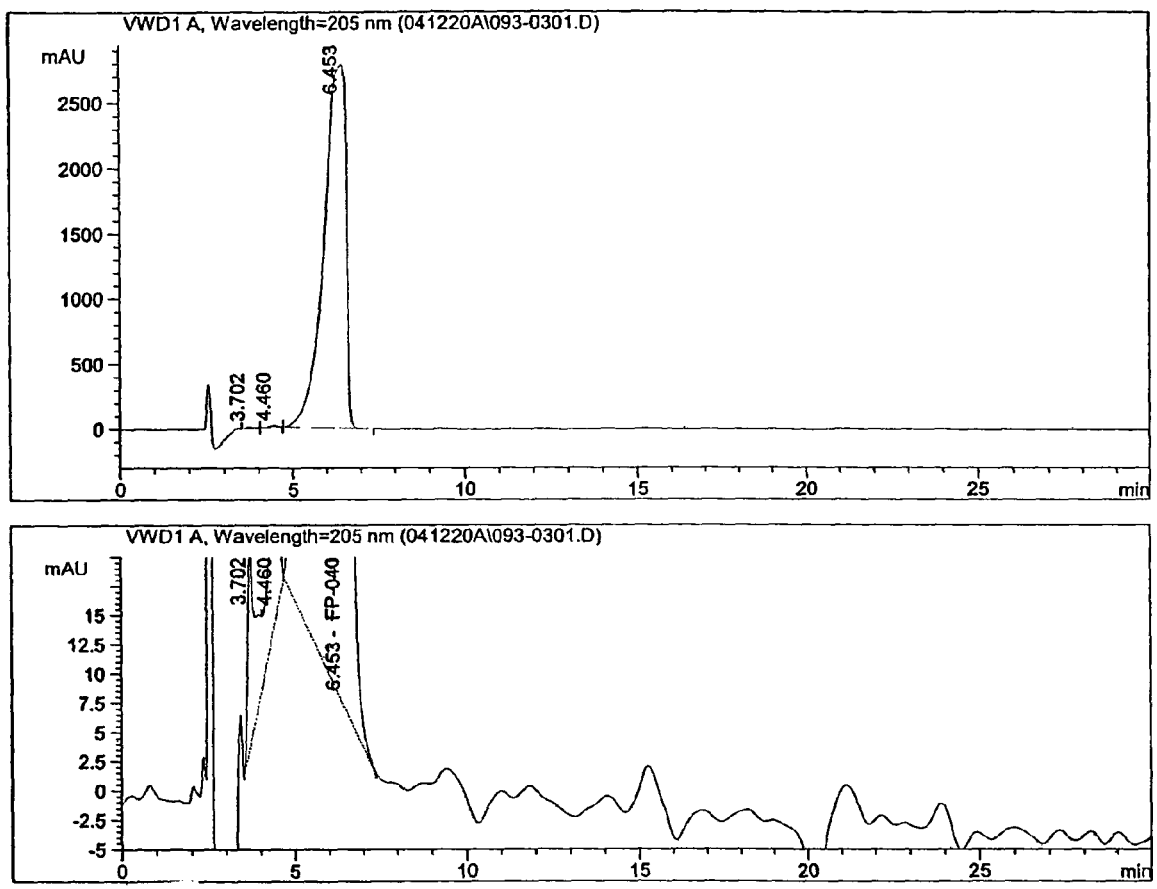
FIG. 1. HPLC of purified DGJ after crystallization. The DGJ is over 99.5% pure.

The term 'alkyl' refers to a straight or branched C1-C20 hydrocarbon group consisting solely of carbon and hydrogen atoms, containing no unsaturation, and which is attached to the rest of the molecule by a single bond, e.g., methyl, ethyl, n-propyl, 1-methylethyl (isopropyl), n-butyl, n-pentyl, 1,1-dimethylethyl (t-butyl). The alkyls used herein are preferably C1-C8 alkyls.

The term "alkenyl" refers to a C2-C20 aliphatic hydrocarbon group containing at least one carbon-carbon double bond and which may be a straight or branched chain, e.g., ethenyl, 1-propenyl, 2-propenyl (allyl), iso-propenyl, 2-methyl-1-propenyl, 1-butenyl, 2-butenyl.

The term "cycloalkyl" denotes an unsaturated, non-aromatic mono- or multicyclic hydrocarbon ring system such as cyclopropyl, cyclobutyl, cyclopentyl, cyclohexyl. Examples of multicyclic cycloalkyl groups include perhydronapthyl, adamantyl and norbornyl groups bridged cyclic group or spriirobicyclic groups, e.g., spiro (4,4) non-2-yl.

The term "cycloalkalkyl" refers to a cycloalkyl as defined above directly attached to an alkyl group as defined above, which results in the creation of a stable structure such as cyclopropylmethyl, cyclobutylethyl, cyclopentylethyl.

The term "alkyl ether" refers to an alkyl group or cycloalkyl group as defined above having at least one oxygen incorporated into the alkyl chain, e.g., methyl ethyl ether, diethyl ether, tetrahydrofuran.

The term "alkyl amine" refers to an alkyl group or a cycloalkyl group as defined above having at least one nitrogen atom, e.g., n-butyl amine and tetrahydrooxazine.

The term "aryl" refers to aromatic radicals having in the range of about 6 to about 14 carbon atoms such as phenyl, naphthyl, tetrahydronapthyl, indanyl, and biphenyl.

The term "arylalkyl" refers to an aryl group as defined above directly bonded to an alkyl group as defined above, e.g., —CH2C6H5, and —C2H4C6H5.

The term "heterocyclic" refers to a stable 3- to 15-membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl.

The heterocyclic ring radical may be attached to the main structure at any heteroatom or carbon atom that results in the creation of a stable structure.

The term "heteroaryl" refers to a heterocyclic ring wherein the ring is aromatic.

The term "heteroarylalkyl" refers to heteroaryl ring radical as defined above directly bonded to alkyl group. The heteroarylalkyl radical may be attached to the main structure at any carbon atom from alkyl group that results in the creation of a stable structure.

The term "heterocyclyl" refers to a heterocylic ring radical as defined above. The heterocyclyl ring radical may be attached to the main structure at any heteroatom or carbon atom that results in the creation of a stable structure.

The term "heterocyclylalkyl" refers to a heterocylic ring radical as defined above directly bonded to alkyl group. The heterocyclylalkyl radical may be attached to the main structure at carbon atom in the alkyl group that results in the creation of a stable structure.

The substituents in the 'substituted alkyl', 'substituted alkenyl' 'substituted alkynyl' 'substituted cycloalkyl' 'substituted cycloalkalkyl' 'substituted cycloalkenyl' 'substituted arylalkyl' 'substituted aryl' 'substituted heterocyclic ring', 'substituted heteroaryl ring,' 'substituted heteroarylalkyl', or 'substituted heterocyclylalkyl ring', may be the same or different with one or more selected from the groups hydrogen, hydroxyl, halogen, carboxyl, cyano, amino, nitro, oxo (=O), thio (=S), or optionally substituted groups selected from alkyl, alkoxy, alkenyl, alkynyl, aryl, arylalkyl, cycloalkyl, aryl, heteroaryl, heteroarylalkyl, heterocyclic ring, —CO-ORx, —C(O)Rx, —C(S)Rx, —C(O)NRxRy, —C(O)ON-RxRy, —NRxCONRyRz, —N(Rx)SORy, —N(Rx)SO2Ry, —(=N—N(Rx)Ry), —NRxC(O)ORy, —NRxRy, —NRxC(O)Ry—, —NRxC(S)Ry —NRxC(S)NRyRz, —SON-RxRy—, —SO2NRxRy—, —ORx, —ORxC(O)NRyRz, —ORxC(O)ORy—, —OC(O)Rx, —OC(O)NRxRy, —RxN-RyRz, —RxRyRz, —RxCF3, —RxNRyC(O)Rz, —RxORy, —RxC(O)ORy, —RxC(O)NRyRz, —RxC(O)Rx, —RxOC(O)Ry, —SRx, —SORx, —SO2Rx, —ONO2, wherein Rx, Ry and Rz in each of the above groups can be hydrogen atom, substituted or unsubstituted alkyl, haloalkyl, substituted or unsubstituted arylalkyl, substituted or unsubstituted aryl, substituted or unsubstituted cycloalkyl, substituted or unsubstituted cycloalkalkyl substituted or unsubstituted heterocyclic ring, substituted or unsubstituted heterocyclylalkyl, substituted or unsubstituted heteroaryl or substituted or unsubstituted heteroarylalkyl.

The term "halogen" refers to radicals of fluorine, chlorine, bromine and iodine.

The nitrogen-containing sugars may be pentose, hexose, or heptose sugars having at least one oxygen-containing group replaced by a nitrogen-containing group. In one preferred embodiment, the sugar is a hexose sugar.

The nitrogen-containing sugars which may be purified in accordance with the invention can be described by either of the following formulas:

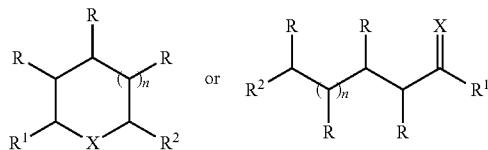

wherein X is NH, O, NHR$^3$, or N(R$^3$)$_2$; each R is independently OH, NH$_2$, NHR$^3$ or N(R$^3$)$_2$; R$^1$ is H, OH, or R$_1$ links, through —O, to another sugar; and R$_2$ is H, CH$_3$, CH$_2$OH, or R$^2$ links, through —CH$_2$—O—, to another sugar, and each R$^3$ is independently H or a substituted or unsubstituted C$_1$-C$_{12}$ alkyl, C$_2$-C$_{12}$ alkenyl, C$_2$-C$_{12}$ alkynyl, C$_5$-C$_6$ cycloalkyl, C$_5$-C$_{12}$ cycloalkenyl, C$_5$-C$_{12}$ aryl, C$_4$-C$_{12}$ heteroaryl, C$_6$-C$_{12}$ arylalkyl, C$_4$-C$_{12}$ heterocyclyl, C$_6$-C$_{12}$ hetero-cyclic-alkyl, C$_5$-C$_{12}$ heteroarylalkyl or a C$_2$-C$_{12}$ acyl and n is 0, 1, or 2. The process described herein can be used to separate polar inorganic chloride salts from polar amino- or imino-sugars. The presence of one or more imino or amino group in the sugar makes the sugar soluble in the HCl. Therefore, when X is O, at least one R must be NH$_2$ or NHR$^3$ or N(R$^3$)$_2$. There may be two or more independent NH, NH$_2$, NHR$^3$, or N(R$^3$)$_2$ moieties at X and/or R position(s).

Polar inorganic chloride salts are not soluble in concentrated hydrochloric acid due to common ion effect. The common ion effect occurs when a soluble salt containing an ion common to a slightly soluble salt are mixed and the equilibrium of the slightly soluble salt is changed because of the increased concentration of the common ion. According to LeChatelier's Principle, the stress (added concentration) placed on the slightly soluble salt equilibria will shift the equilibria to reduce the common ion concentration and thereby reducing the solubility of the slightly soluble salt.

Amino- and imino-sugars constitute a major class of naturally occurring molecules have important and diverse biological functions. (R. W. Jeanloz, Academic Press, New York, 1969.) Many are naturally occurring, particularly as components of various antibiotics and other important biomolecules. The amino- and imino-sugars may exist as glycosides, and may be purified by the method described herein. These natural glycosides contain a sugar (glycone) and a biologically active component (aglycone). These amino- or imino-sugars include the glucose analogue, nojirimycin, which has been found in a *Streptomyces* filtrate and 1-deoxynojirimycin (DNJ), which has been found in mulberry leaves. Other natural hexose amino- or imino-sugars have been systematically described as derivatives of these parent heterocyclic compounds or sugars, e.g. 1-deoxynojirimycin (2S-hydroxymethyl-3R,4R,5S-trihydroxy-piperidine or 1,5-dideoxy-1,5-imino-D-glucitol). There are a variety of synthesis route for making these sugars in addition to isolation from biological sources. For example, DGJ has been synthesized from D-glucose (Legler G, et al., *Carbohydr. Res.* 1986 Nov. 1; 155:119-29); D-galactose (Uriel, C., Santoyo-Gonzalez, F., et al., *Synlett* 1999 593-595; *Synthesis* 1998 1787-1792); galactopyranose (Bernotas R C, et al., *Carbohydr. Res.* 1987 Sep. 15; 167:305-11); L-tartaric acid (Aoyagi et al., *J. Org. Chem.* 1991, 56, 815); quebrachoitol (Chida et al., *J. Chem. Soc., Chem Commun.* 1994, 1247); galactofuranose (Paulsen et al., *Chem. Ber.* 1980, 113, 2601); benzene (Johnson et al., *Tetrahedron Lett.* 1995, 36, 653); arabino-hexos-5-ulose (Barili et al., tetrahedron 1997, 3407); 5-azido-1,4-lactones (Shilvock et al., Synlett, 1998, 554); deoxynojirimycin (Takahashi et al., *J. Carbohydr. Chem.* 1998, 17, 117); acetylglucosamine (Heightman et al., *Helv. Chim.* Acta 1995, 78, 514); myo-inositol (Chida N, et al., *Carbohydr. Res.* 1992 Dec. 31; 237:185-94); dioxanylpiperidene (Takahata et al., *Org. Lett.* 2003; 5(14); 2527-2529); and (E)-2,4-pentadienol (Martin R, et al., *Org Lett.* 2000 January; 2(1):93-5) (Hughes A B, et al., *Nat Prod Rep.* 1994 April; 11(2):135-62). Synthesis of N-methyl-1-deoxynojirimycin-containing oligosaccharides is described by Kiso (*Bioorg Med Chem.* 1994 November; 2(11): 1295-308) where protected 1-deoxynojirimycin derivative was coupled with methyl-1-thioglycosides (glycosyl donors) of D-galactose and triflate in the presence of a glycosyl promoter.

Second generation sugars can also be purified by the method of the present invention. These compounds have greatly improved specificity for glycosidase inhibition and fewer or less intense side effects (e.g., gastrointestinal problems). A non-limiting list of sugars that may be purified using the method provided herein included in Table I.

TABLE I

| Nitrogen Containing Hexose Sugars | |
|---|---|
| D-1-deoxygalactonojirimycin (DGJ) | α-Homoallonojirimycin (α-allo-HNJ) |
| Castanospermine | α-Homogalactonojirimycin (α-galacto-HNJ) |
| Swainsonine | N-Methyl-1-deoxygalactonojirimycin (N-Me-DGJ) |
| 1-Deoxynojirimycin (DNJ) | N-Ethyl-1-deoxygalactonojirimycin (N-Et-DGJ) |
| 1-Deoxymannojirimycin (manno-DNJ) | N-Propyl-1-deoxygalactonojirimycin (N-Pr-DGJ) |
| 1-Deoxy-3-epi-nojirimycin (allo-DNJ) | N-Butyl-1-deoxygalactonojirimycin (N-Bu-DGJ) |
| 1,2-Dideoxygalactonojirimycin | N-Hydroxyethyl-1-deoxygalactonojirimycin (N-HE-DGJ) |
| α-Homonojirimycin (α-HNJ) | β-1-C-Butyl-deoxygalactonojirimycin |
| α-Homomannojirimycin (α-manno-HNJ) | |

The synthesis and isolation of these crude compounds are known, and can be found, for example, in U.S. Pat. Nos. 4,861,892; 4,894,388; 4,910,310; 4,996,329; 5,011,929; 5,013,842; 5,017,704; 5,580,884; 5,286,877; 5,100,797; 6,291,657, and 6,599,919. The syntheses of a variety of deoxynojirimycin (DNJ) derivatives are described in U.S. Pat. Nos. 5,622,972; 5,200,523; 5,043,273; 4,944,572; 4,246,345; 4,266,025; 4,405,714; and 4,806,650 and in U.S. application Ser. No. 10/031,145. Additional sugar compounds and their synthesis are disclosed in Jacob, G. S., et al., *Cur. Opin. Struct. Biol.* (1995) 5:605-611, and Winchester, B., et al., *Glycobiol* (1992) 2:199-210. Additional methods for the synthesis of amino sugars are described in, for example: A. Golebiowski, J. Jurczak, *Synlett* 241, 1992; J. Du Bois, et al. *J. Am. Chem. Soc.* 119:3179, 1997; K. C. Nicolaou, et al. *Angew. Chem. Int. Ed. Engl.*, 39:2525, 2000.

After synthesis, the sugars described herein will normally contain impurities of alkali- or alkali earth-containing compound, such as sodium methoxide, which must be removed.

One amino-sugar of particular interest for purification by the method of the current invention is DGJ. DGJ, or D-1-deoxygalactonojirimycin, also described as (2R,3S,4R,5S)-2-hydroxymethyl-3,4,5-trihydroxypiperidine and 1-deoxygalactostatin, is a nojirimycin (5-amino-5-deoxy-D-galactopyranose) derivative of the form:

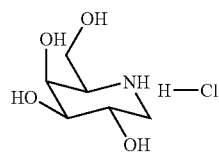

A concentrated hydrochloric acid extraction can be used to separate the residual NaCl or other salts and impurities from a DGJ product. DGJ is not degraded or dehydrated in these conditions and sodium chloride is completely removed in one simple filtration. By extracting the DGJ using concentrated HCl and crystallizing, the DGJ product exhibits excellent purity and crystal structure.

Concentrated HCl dissolves the sugar (e.g., DGJ hydrochloride), and not NaCl or other metal salt contaminants, allowing for the separation of the DGJ from the salt. This is at least in part due to the common ion effect playing a significant role in the insolubility of the NaCl. DGJ is stable in the concentrated HCl and does not dehydrate, as it would in other strong acid, such as $H_2SO_4$. In one embodiment, a crude DGJ salt is extracted from mixture with concentrated hydrochloric acid leaving NaCl undissolved. After filtration, DGJ.HCl can be precipitated, for example, by pouring the acidic solution into a solution of tetrahydrofuran/diethyl ether. The DGJ salt may be formed before solvation with concentrated HCl, or it may be formed during addition of concentrated HCl.

The procedure described above can be also modified in such a way that the sugar is first added to water instead of concentrated hydrochloric acid, and the solution is then saturated with hydrogen chloride gas.

The amino- or imino-sugar is stable for hours to days in the concentrated HCl, allowing for completion of the work-up at any scale without degradation of the imino-sugar.

2-Amino Glucose

Other sugars of particular interest for purification by the method of the current invention include 2-amino glucose, which is commonly known as glucosamine, and derivatives thereof. 2-amino glucose can be isolated or synthesized by methods known in the art. For example, 2-amino-2-deoxy-D-glucose can be made by the method of Meyer zu Reckendorf (*Chem Ber.* 1969; 102(3):1076-9), by irradiation of D-glucose and amino acids (Doner L W, et al., *Carbohydr. Res.* 1976 April; 47(2):342-4), and by using violuric acid (Moulik S P, et al., *Carbohydr. Res.* 1972 November; 25(1):197-203). After synthesis by known techniques, the crude 2-amino glucose is dissolved in concentrated HCl that has first been heated. This allows for the purification of the sugar by removal of the non-solvated Na+ or other metal ion impurities and crystallization of the product.

After filtering of the hydrochloric acid amino- or imino-sugar solution, from inorganic insoluble salts, the amino- or imino-sugar can be isolated without any additional handling (e.g. removal of the solvent by concentration) by diluting with solvents and solvent mixtures miscible with concentrated hydrochloric acid, for example, tetrahydrofuran, ethanol, acetone, or tetrahydrofuran/diethyl ether and resulting crystallization. Other solvents and solvent mixtures may be used as well. After this operation crystallization may be repeated using other solvents and solvent mixtures, e.g. water/ethanol for DGJ.HCl. The yield of DGJ.HCl purification, including two crystallizations from water/ethanol, is about 80%.

The term "impurity" as used herein denotes any component in the nitrogen-containing sugar that is undesirable in the final product. The term "contaminated" means that an impurity exists in the contaminated sample. As used herein "concentrated HCl" refers to a solution having at least 35% HCl. As used herein, the terms "multi-kilogram," "multi-kg," and "preparatory scale" denote a scale of synthesis where the product is produced in an amount greater than one kg, in a single pass.

EXAMPLES

The present invention is further illustrated in the following examples, which should not be taken to limit the scope of the invention.

Example 1

Preparation and Purification of DGJ

A protected crystalline galactofuranoside obtained from the technique described by Santoyo-Gonzalez. 5-azido-5-deoxy-1,2,3,6-tetrapivaloyl-α-D-galactofuranoside (1250 g), was hydrogenated for 1-2 days using methanol (10 L) with palladium on carbon (10%, wet, 44 g) at 50 psi of $H_2$. Sodium methoxide (25% in methanol, 1.25 L) was added and hydrogenation was continued for 1-2 days at 100 psi of $H_2$. Catalyst was removed by filtration and the reaction was acidified with methanolic hydrogen chloride solution (20%, 1.9 L) and concentrated to give crude mixture of DGJ.HCl and sodium chloride as a solid. The purity of the DGJ was about 70% (w/w assay), with the remaining 30% being mostly sodium chloride.

Figure 2A:
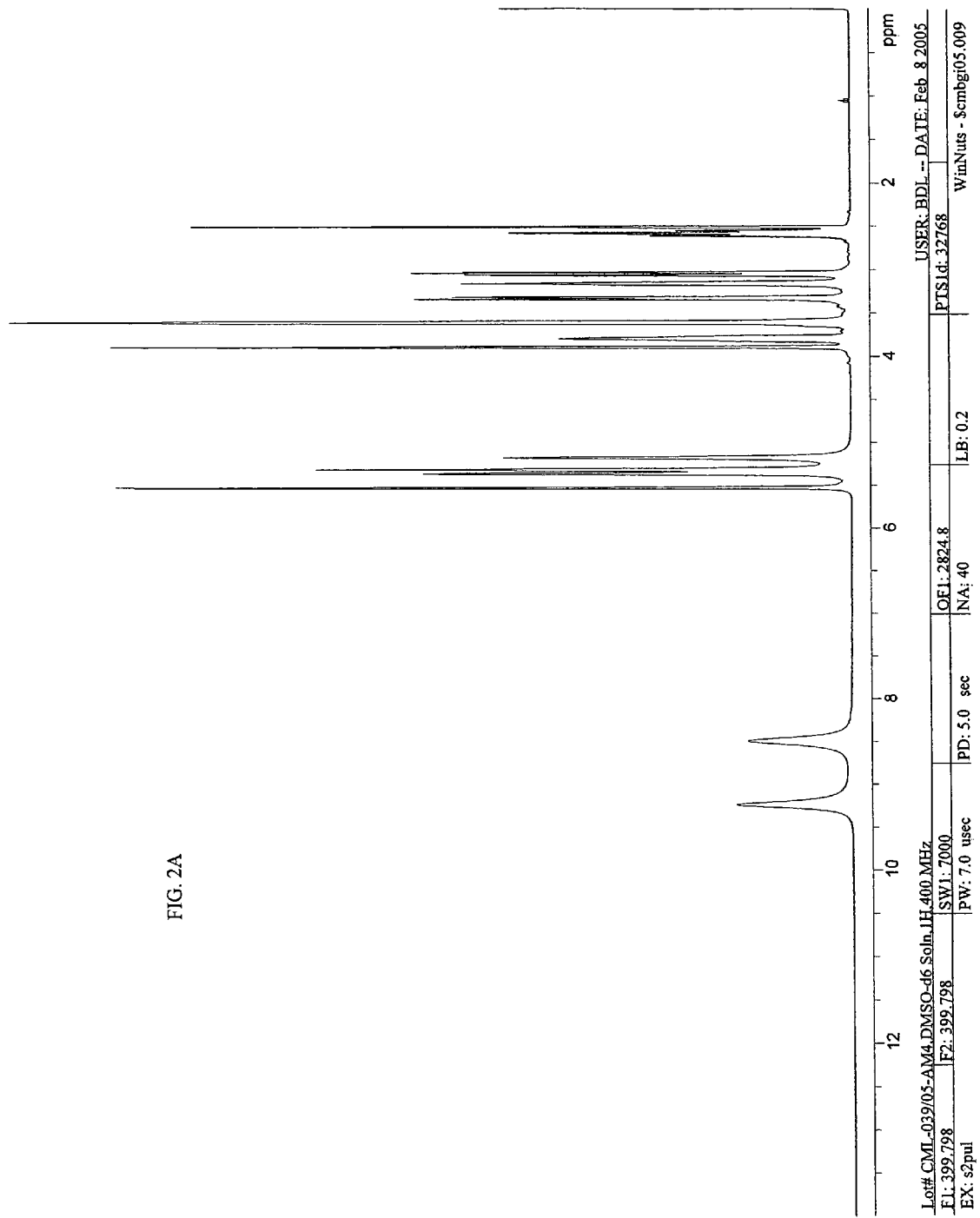
FIG. 2A. $^1$H NMR of DGJ (post HCl extraction and crystallization), from 0-15 ppm in DMSO.
Figure 2B:
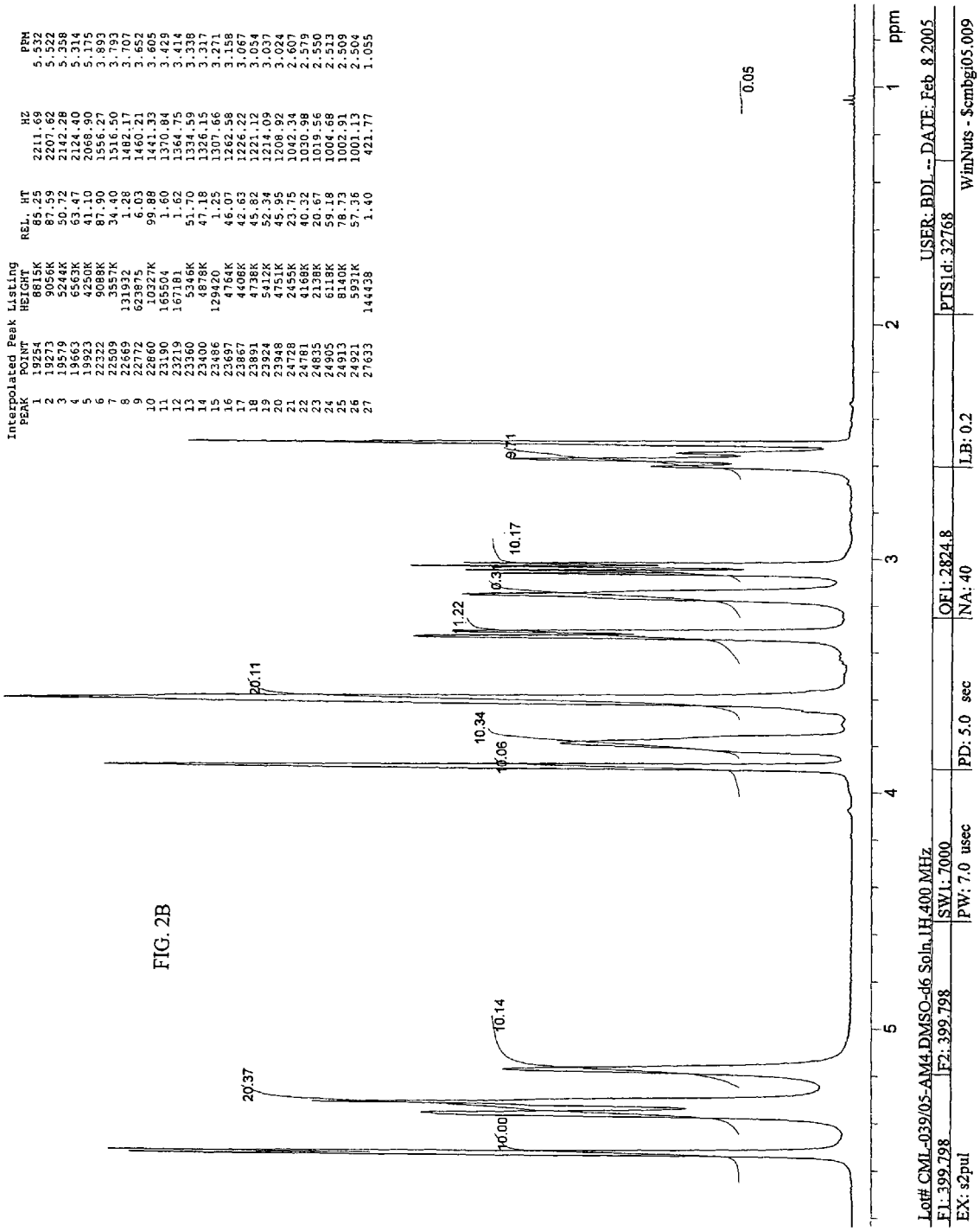
FIG. 2B. $^1$H NMR of DGJ (post HCl extraction and crystallization), from 0-5 ppm, in DMSO.
Figure 3A:
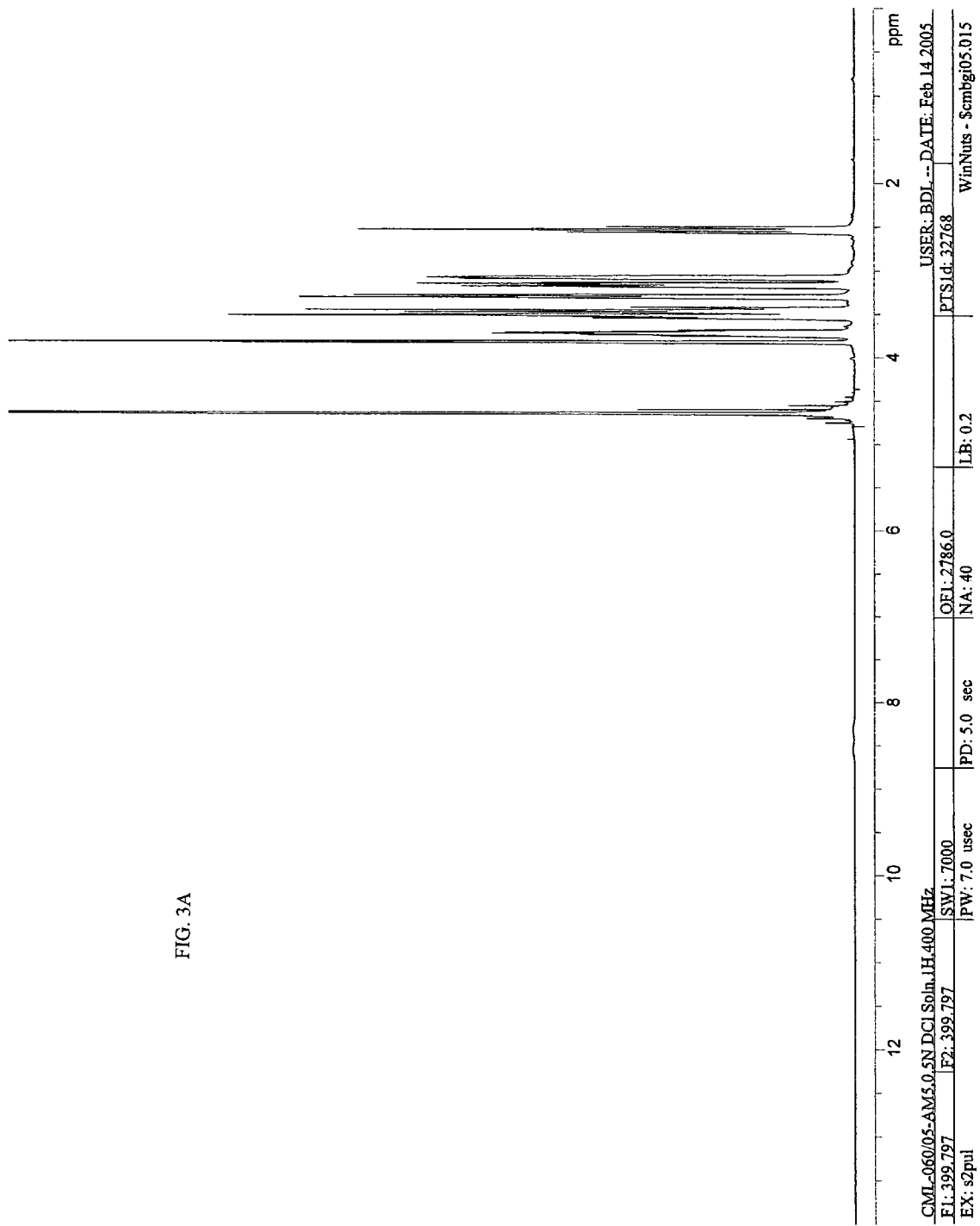
FIG. 3A. ¹H NMR of purified DGJ (after recrystallization), from 0-15 ppm, in $D_2O$. Note OH moiety has exchanged with OD.
Figure 3B:
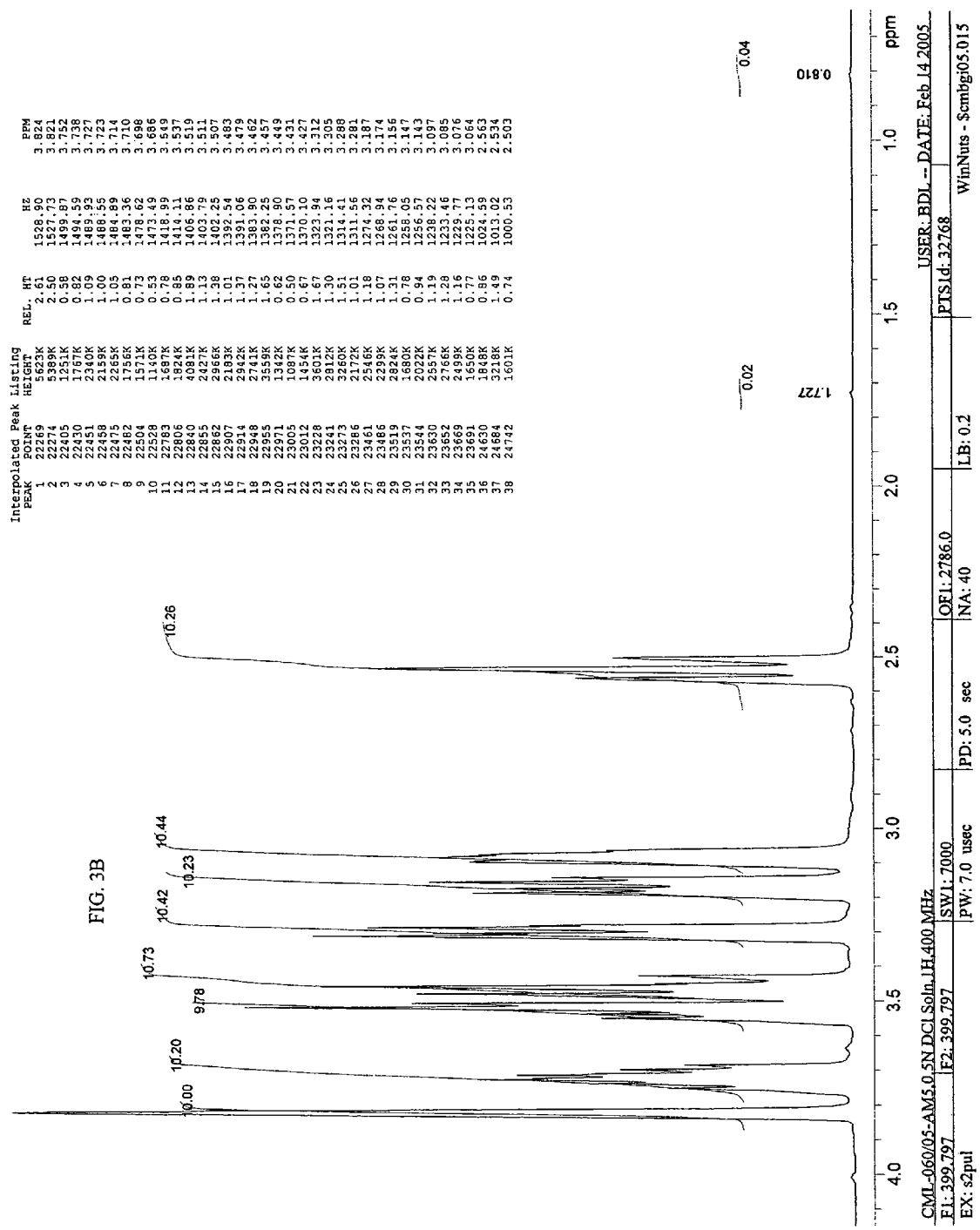
FIG. 3B. ¹H NMR of purified DGJ (after recrystallization), from 0-4 ppm, in $D_2O$. Note OH moiety has exchanged with OD.
Figure 4:
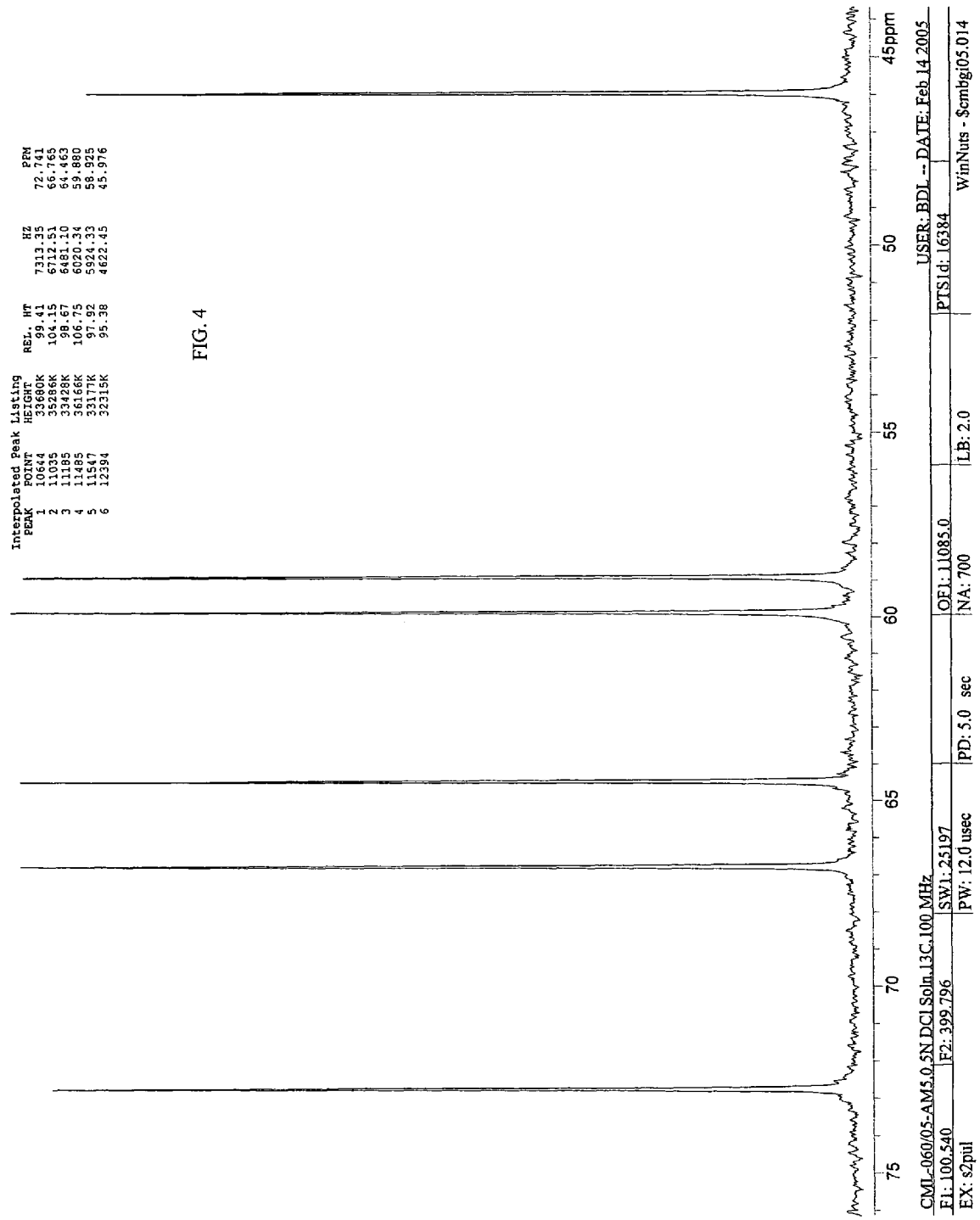
FIG. 4. ¹³C NMR of purified DGJ, (after recrystallization), 45-76 ppm.

The solid was washed with tetrahydrofuran (2×0.5 L) and ether (1×0.5 L), and then combined with concentrated hydrochloric acid (3 L). DGJ went into solution, leaving NaCl undissolved. The obtained suspension was filtered to remove sodium chloride; the solid sodium chloride was washed with additional portion of hydrochloric acid (2×0.3 L). All hydrochloric acid solution were combined and slowly poured into stirred solution of tetrahydrofuran (60 L) and ether (11.3 L). The precipitate formed while the stirring was continued for 2 hours. The solid crude DGJ.HCl, was filtered and washed with tetrahydrofuran (0.5 L) and ether (2×0.5 L). An NMR spectrum is shown in FIGS. 2A-2B.

The solid was dried and recrystallized from water (1.2 mL/g) and ethanol (10 ml/1 ml of water). This recrystallization step may be repeated. This procedure gave white crystalline DGJ.HCl, and was usually obtained in about 70-75% yield (320-345 g). The product of the purification, DGJ.HCl is a white crystalline solid, HPLC>98% (w/w assay) as shown in FIG. 1. FIGS. 3A-3D and FIG. 4 show the NMR spectra of purified DGJ, showing the six sugar carbons.

Example 2

Purification of 1-deoxymannojirimycin 1-deoxymannojirimycin is made by the method described by Mariano (J. Org. Chem., 1998, 841-859, see pg. 859, herein incorporated by reference). However, instead of purification by ion-exchange resin as described by Mariano, the 1-deoxymannojirimycin is mixed with concentrated HCl. The suspension is then filtered to remove the salt and the 1-deoxymannojirimycin hydrochloride is precipitated crystallized using solvents known for recrystallization of 1-deoxymannojirimycin (THF for crystallization and then ethanol/water.

Example 3

Purification of (+)-1-deoxynojirimycin (+)-1-deoxynojirimycin is made by the method Kibayashi et al. (J. Org. Chem., 1987, 3337-3342, see pg. 3341, herein incorporated by reference). It is synthesized from a piperidine compound (#14) in HCl/MeOH. The reported yield of 90% indicates that the reaction is essentially clean and does not contain other sugar side products. Therefore, the column chromatography used by Kibayashi is for the isolation of the product from non-sugar related impurities. Therefore, instead of purification by silica gel chromatography, the (+)-1-deoxynojirimycin is mixed with concentrated HCl. The suspension is then filtered to remove the salt and the nojirimycin is crystallized using solvents known for recrystallization of nojirimycin.

Example 4

Purification of Nojirimycin

Nojirimycin is made by the method described by Kibayashi et al. (J. Org. Chem., 1987, 3337-3342, see pg. 3342). However, after evaporating of the mixture at reduced pressure, instead of purification by silica gel chromatography with ammonia-methanol-chloroform as described by Kibayashi, the nojirimycin is mixed with concentrated HCl. The suspension is then filtered to remove the impurities not dissolved in HCl and the nojirimycin is crystallized using solvents known for recrystallization of nojirimycin.

Many variations of the present invention will suggest themselves to those skilled in the art in light of the above detailed description. All such obvious variations are within the fully intended scope of the appended claims.

Those of skill in the art should, in light of the present disclosure, appreciate that many changes can be made in the specific embodiments where are disclosed herein and still obtain a like or similar result without departing from the spirit and scope of the invention.

The above-mentioned patents, applications, test methods, publications are hereby incorporated by reference their entirety.

We claim:

1. A method for the purification of a crude D-1-deoxygalactonojirimycin contaminated with an alkali- or alkali earth metal-containing compound comprising:
   (a) admixing
   D-1-deoxygalactonojirimycin with a solution having at least 35% hydrochloric acid or with hydrogen chloride gas to saturation to form a chloride salt of the alkali- or alkali earth metal-containing compound;
   (b) forming the chloride salt of the alkali- or alkali earth metal-containing compound;
   (c) removing the chloride salt of the alkali- or alkali earth metal-containing compound wherein the chloride salt is a solid; and
   (d) crystallizing D-1-deoxygalactonojirimycin by addition of a solvent miscible with hydrochloric acid.

2. The method of claim 1, wherein D-1-deoxygalactonojirimycin is mixed with water and then saturated with hydrogen chloride gas.

3. The method of claim 1, wherein D-1-deoxygalactonojirimycin is mixed with a solution having at least 35% hydrochloric acid.

4. The method of claim 1, wherein the alkali- or alkali earth metal-containing compound was formed from the addition of sodium methoxide.

5. The method of claim 1, wherein crystallizing D-1-deoxygalactonojirimycin comprises adding a water/ethanol solvent mixture.

6. The method of claim 1, wherein the amount of metal-containing compound is reduced to less than 0.01% by weight following step (d).

7. The method of claim 1, wherein D-1-deoxygalactonojirimycin is at least 98% pure following step (d).

8. The method of claim 1, wherein D-1-deoxygalactonojirimycin is at least 99% pure following step (d).

9. The method of claim 1, wherein at least 5 kg of D-1-deoxygalactonojirimycin is produced following purification.

10. The method of claim 1, further comprising synthesizing D-1-deoxygalactonojirimycin from a sugar starting material.

11. A method for purification of a crude D-1-deoxygalactonojirimycin or the HCl salt thereof contaminated with an alkali- or alkali earth metal-containing compound comprising:
   (a) admixing the crude D-1-deoxygalactonojirimycin or the HCl salt thereof with a solution having at least 35% hydrochloric acid or with hydrochloric gas to saturation to form a chloride salt of the alkali- or alkali earth metal-containing compound;
   (b) forming the chloride salt of the alkali- or alkali earth metal-containing compound;
   (c) removing the chloride salt of the alkali- or alkali earth metal-containing compound; and
   (d) crystallizing D-1-deoxygalactonojirimycin.HCl.

12. The method of claim 11, wherein crystallizing D-1-deoxygalactonojirimycin.HCl comprises adding a water/ethanol solvent mixture.

13. The method of claim 11, wherein D-1-deoxygalactonojirimycin.HCl is at least 98% pure following step (d).

14. The method of claim 11, wherein D-1-deoxygalactonojirimycin.HCl is at least 99% pure following step (d).

15. The method of claim 11, further comprising synthesizing D-1-deoxygalactonojirimycin.HCl from a sugar starting material.

16. The method of claim 15, where the sugar starting material is a galactose.

17. The method of claim 1, further comprising removing the chloride salt of the alkali- or alkali earth metal-containing compound by filtration.

18. The method of claim 11, further comprising removing the chloride salt of the alkali- or alkali earth metal-containing compound by filtration.

19. The method of claim 1, wherein the crude D-1-deoxygalactonojirimycin is a 5-amino-5-deoxy-D-galactopyranose derivative of the form:

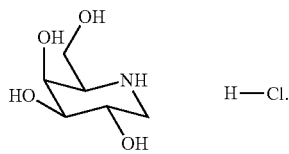

20. The method of claim 11, wherein the D-1-deoxygalactonojirimycin or the HCl salt thereof is admixed with a solution having at least 35% HCl.

* * * * *